United States Patent
Kwon et al.

(10) Patent No.: US 12,153,048 B2
(45) Date of Patent: Nov. 26, 2024

(54) MONOCLONAL ANTIBODY THAT BINDS A MERS-CORONAVIRUS

(71) Applicant: Industry Academic Cooperation Foundation, Hallym University, Chuncheon-si (KR)

(72) Inventors: Hyung Joo Kwon, Cheongju-si (KR); Byoung Kwon Park, Chuncheon-si (KR); Dong Bum Kim, Chuncheon-si (KR)

(73) Assignee: Industry Academic Cooperation Foundation, Hallym University, Chuncheon-si (KR)

( * ) Notice: Subject to any disclaimer, the term of this patent is extended or adjusted under 35 U.S.C. 154(b) by 858 days.

(21) Appl. No.: 17/268,503

(22) PCT Filed: Aug. 13, 2019

(86) PCT No.: PCT/KR2019/010272
§ 371 (c)(1),
(2) Date: Feb. 15, 2021

(87) PCT Pub. No.: WO2020/036403
PCT Pub. Date: Feb. 20, 2020

(65) Prior Publication Data
US 2021/0238261 A1 Aug. 5, 2021

(30) Foreign Application Priority Data

Aug. 17, 2018 (KR) .......................... 10-2018-0096102

(51) Int. Cl.
*C07K 16/08* (2006.01)
*C07K 16/10* (2006.01)
*G01N 33/569* (2006.01)

(52) U.S. Cl.
CPC ... *G01N 33/56983* (2013.01); *C07K 16/1002* (2023.08); *C07K 2317/55* (2013.01); *C07K 2317/56* (2013.01); *C07K 2317/565* (2013.01); *C07K 2317/622* (2013.01); *C07K 2317/92* (2013.01); *G01N 2333/165* (2013.01)

(58) Field of Classification Search
None
See application file for complete search history.

(56) References Cited

U.S. PATENT DOCUMENTS 10,301,377 B2 * 5/2019 Graham ........... G01N 33/56983

OTHER PUBLICATIONS

Vajdos et al. (J. Mol. Biol. 2002, Jul. 5, 320(2):415-428).*
Park et al. Theranostics 11(8): 3853-3867, 2021.*
Park et al. BMP Rep 52(6): 397-402, 2019.*
Du et al. Exp. Opin. Therap. Targets 21(2): 131-143, 2017.*
Li et al. Cell. Res. 25: 1237-1249, 2015.*

* cited by examiner

*Primary Examiner* — Christine J Saoud

(57) ABSTRACT

The present invention relates to a monoclonal antibody specifically recognizing a spike protein of MERS coronavirus (MERS-CoV) or a part of the protein, or a functional fragment thereof, wherein the monoclonal antibody, or functional fragment of the monoclonal antibody characterized in that it comprises polypeptide sequence selected from the group consisting of the following polypeptide sequences: a heavy chain comprising a complementarity determining region 1 (CDR 1) amino acid sequence consisting of the sequence of SEQ ID NO: 1, a CDR2 consisting of the sequence of SEQ ID NO: 2 and a CDR 3 consisting of the sequence of SEQ ID NO: 3; and a light chain comprising CDR1 amino acid sequence consisting of the sequence of SEQ ID NO: 4, a CDR2 consisting of the sequence of SEQ ID NO: 5 and a CDR 3 consisting of the sequence of SEQ ID NO: 6. and uses thereof.

2 Claims, 10 Drawing Sheets
Specification includes a Sequence Listing.

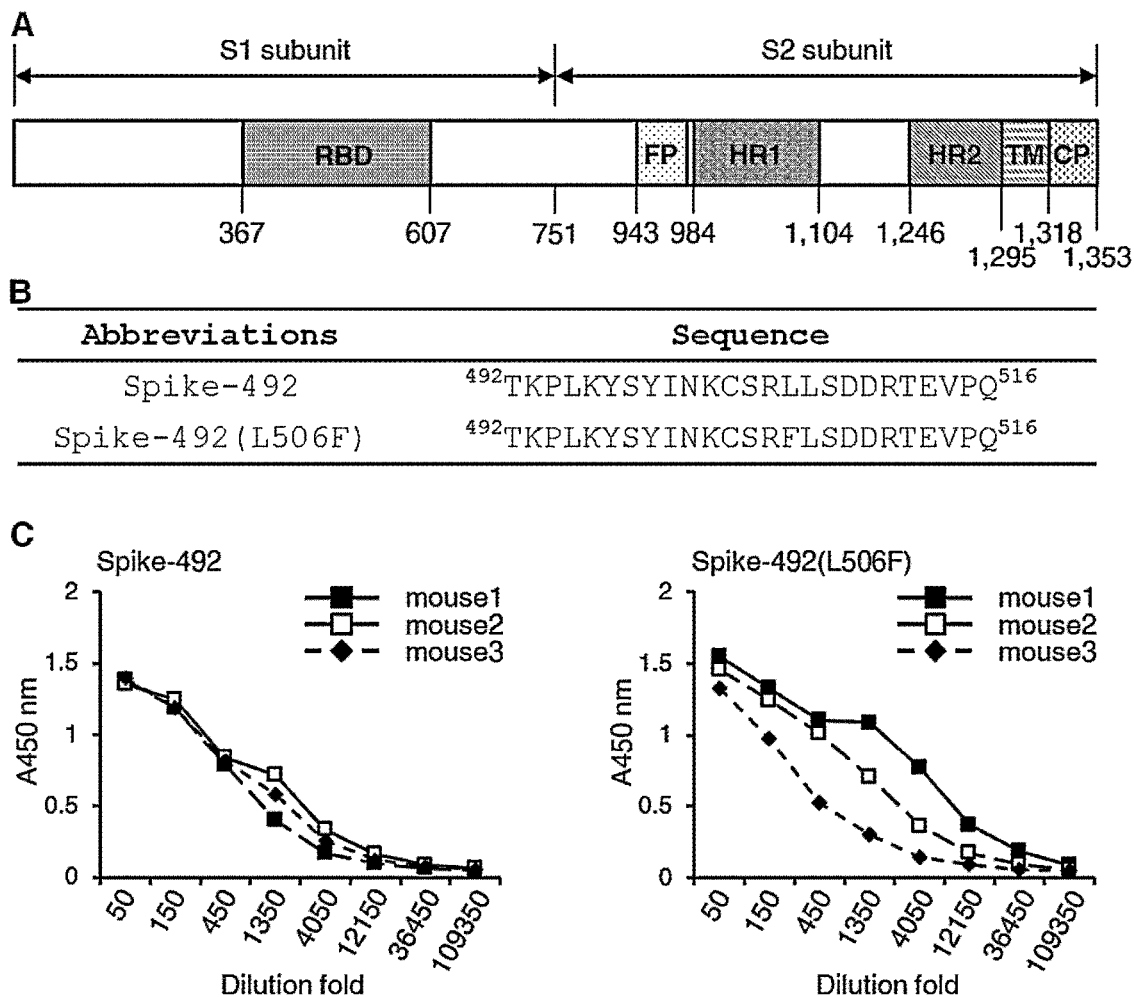
[Fig. 1]

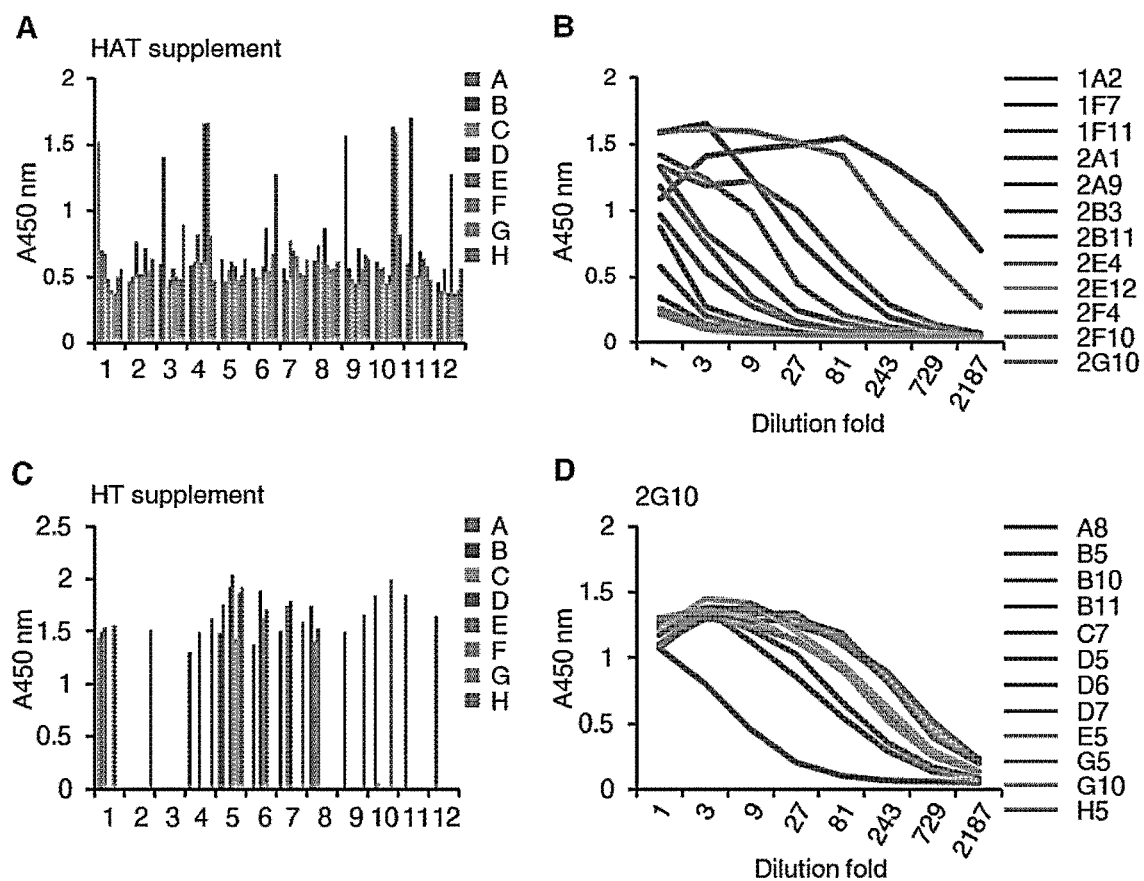
[Fig. 2]

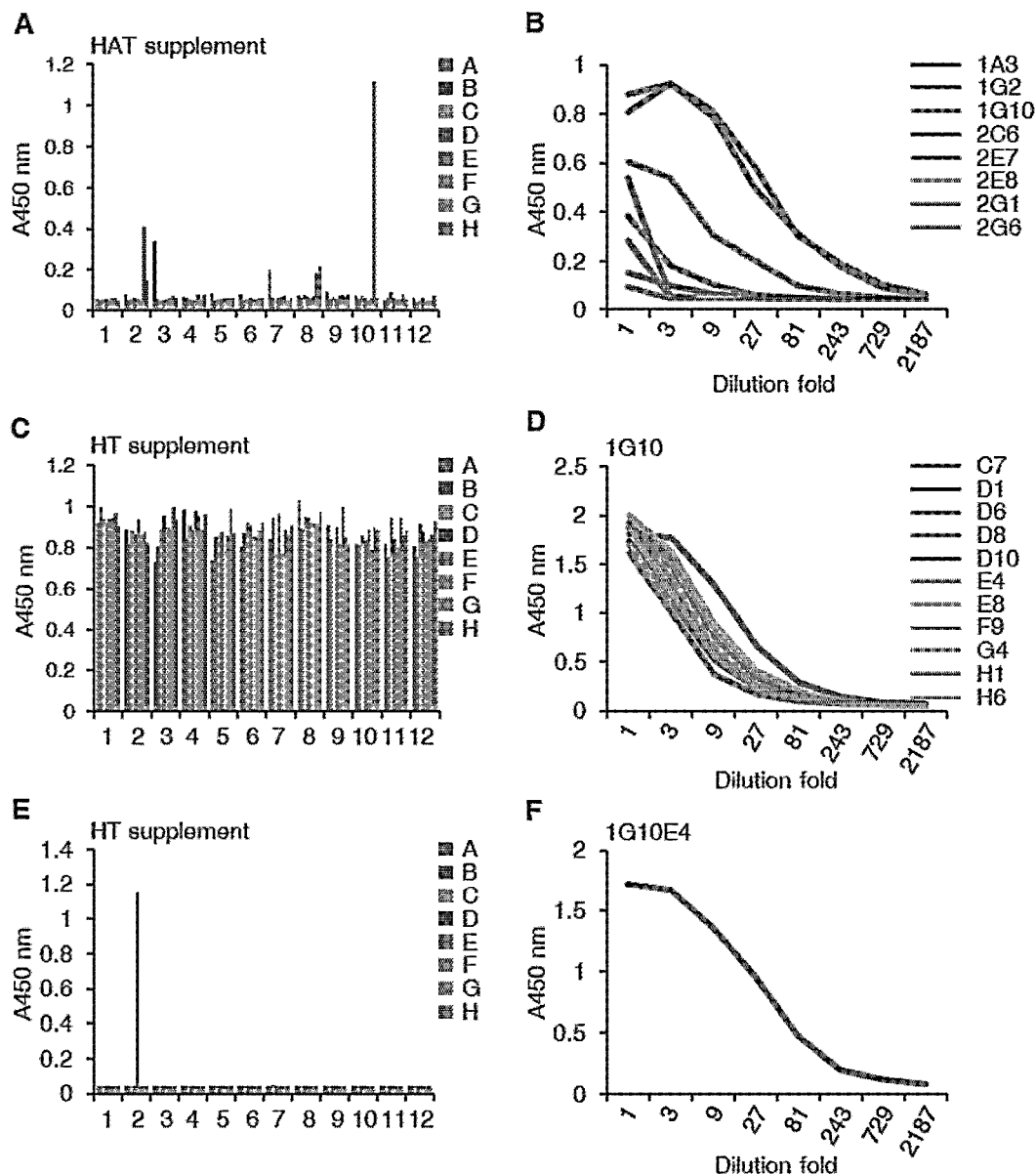
[Fig. 3]

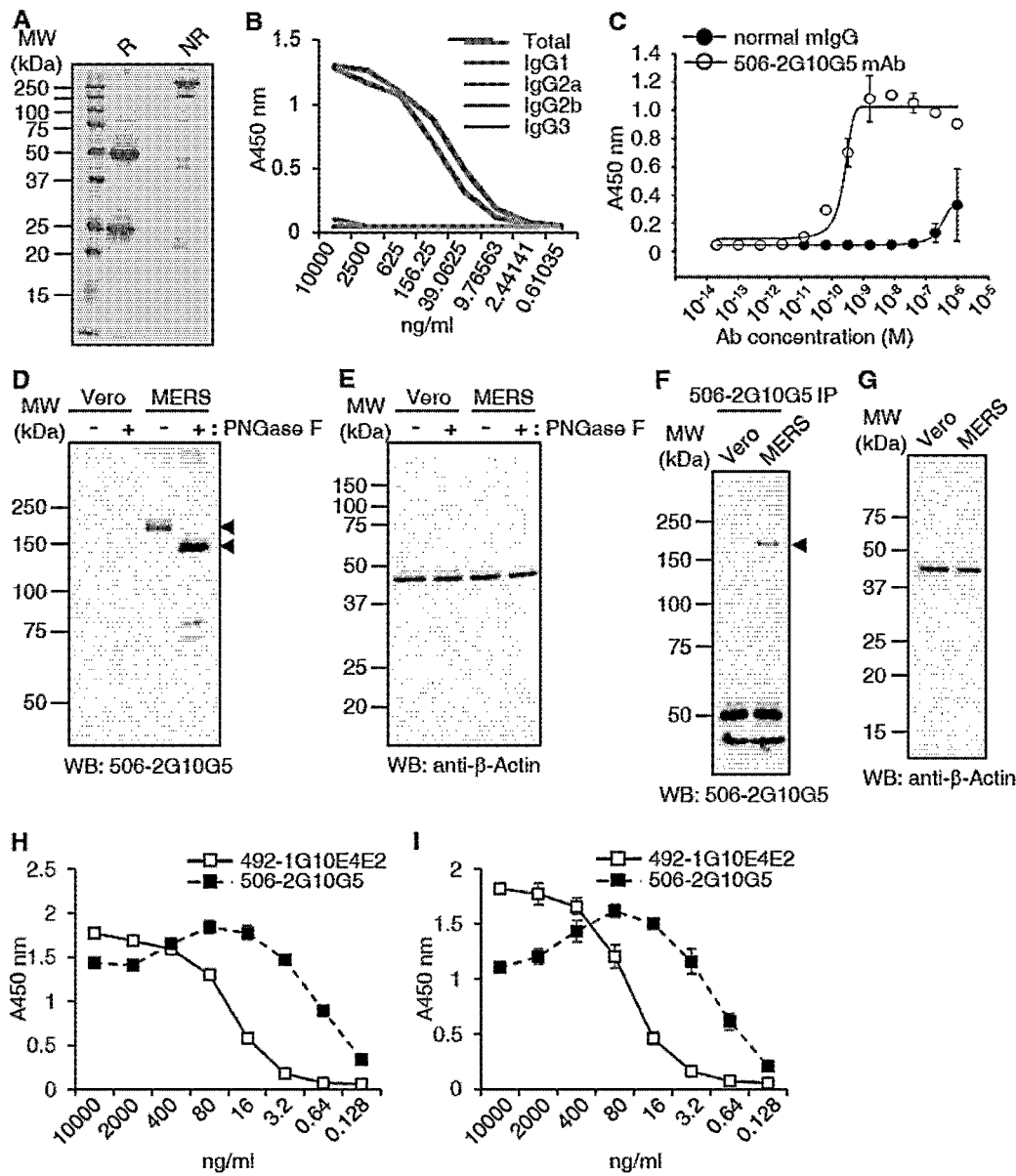
[Fig. 4]

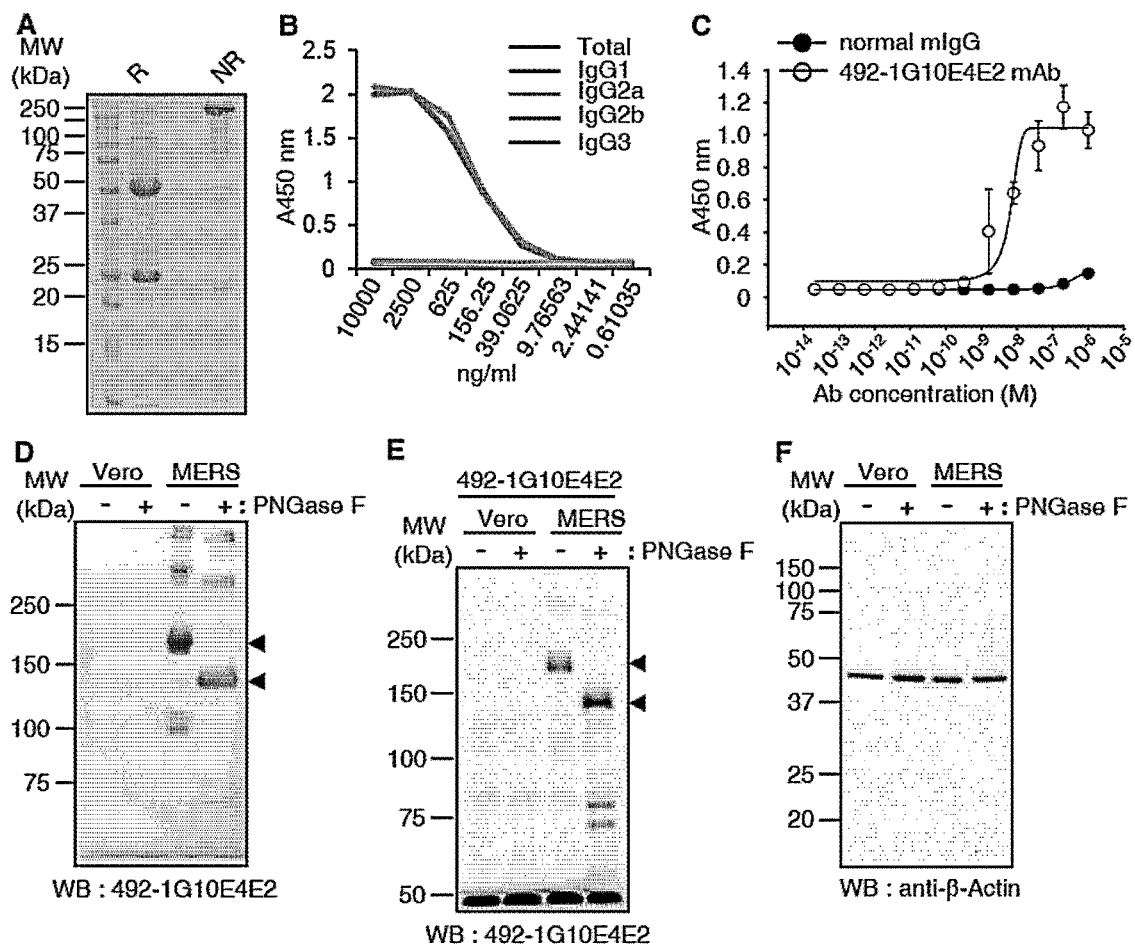
[Fig. 5]

A  Spike506-2G10G5 Heavy chain

CTTCCG GAATTC
CAAGTTAAGCTGCAGGAGTCTGGAGGAGGCTTGGTGCAACCTGGGGGGTCACGGGGACTCTCTTGTGAAGGCTCAGGGTTTA
CTTTTAGTGGCTTCTGGATGAGCTGGGTTCGACAGACACCTGGTAAGACCCTGGAGTGGATTGGAGACATTAATTCTGATGG
CAGTATAATAAACTACGCACCATCCATCAAGGATCGATTCACTATCTTCAGAGACAATGACAAGACCACCCTGTACCTGCAG
ATGAGCAATGTGCGATCTGAGGACACAGCCACGTATTTCTGTTCGATCTACTATGATTCCTGGTTTGCTTACTGGGGCCAAG
GGACTCTGGTCACTGTCTCTGCAGCCAAAACGACACCCCCATCTGTCTAT AGATCT TCC

```
                                    CDR1                        CDR2
                              ┌─────────────┐           ┌─────────────────┐
LPEFQVKLQESGGGLVQPGGSRGLSCEGS GFTFSGFWMS WVRQTPGKTLEWIG DINSDGSIINYAPSIKD RFTIFRDNDKTT
LYLQMSNVRSEDTATYFCSI YYDSWFAY WGQGTLVTVSAAKTTPPSVYRSS
                    └────────┘
                      CDR3
```

B  Spike506-2G10G5 Kappa chain

GG GAGCTC
GATATTGTGCTCACACAGTCTCCACTCTCCCTGCCCGTCAGTCTTGGAGATCAAGCCTCCATCTCTTGCAGATCTAGTCAGAG
CATTGTACATAGCAATGGAAACACCTATTTAGAATGGTACCTGCAGAAACCAGGCCAGTCTCCAAAGCTCCTGATCTACAAAG
TTTCCAACCGATTTTCTGGGGTCCCAGACAGGTTCAGTGGCAGTGGATCAGGGACAGATTTCACACTCAAGATCAGCAGAGTG
GAGGCTGAAGATCTGGGAGTTTATTACTGCTTTCAAGGTTCACATGTTCCTCGGACGTTCGGTGGAGGCACCAAGCTGGAAAT
CAAACGGGCTGATGCTGCACCAACTGTATCC GCATGC ACC

```
                                  CDR1                      CDR2
                           ┌─────────────────────┐      ┌────────┐
ELDIVLTQSPLSLPVSLGDQASISC RSSQSIVHSNGNTYLH WYLQKPGQSPKLLIY KVSNRFS GVPDRFSGSGSGTDFTLKIS
RVEAEDLGVYYC FQGSHVPRT FGGGTKLEIKRADAAPTVSACT
            └──────────┘
              CDR3
```

[Fig. 6]

A Spik492-1G10E4E2 Heavy chain

<u>CTTCCG GAATTC</u>
<u>CAAGTTCAGCTGGAGCAGTCTGGGGCTGAGCTGGTGAGGCCTGGGGCTTCAGTGACGGTGTCCTGCAAGGCTTCGGGCTACACAT
TTACTGACTATGAAATGCACTGGGTGAAGCAGACACCTGTGCATGGCCTGGAATGGATTGGAGCTATTGATCCTGAAACTGGTGG
TACTGCCTACAATCAGAAGTTCAAGGGCAAGGCCACACTGACTGCAGACAAATCCTCCAGCACAGCCTACATGGAGCTCCGCAGC
CTGACATCTGAGGAGTCTGCCGTCTATTACTGTACAAGACCAAGTAGCTACGATGCTATGGACTACTGGGGTCAAGGAACCTCAG
TCACCGTCTCCTCAGCCAAAACAACAGCCCCATCGGTCTATCCACTGGCCCCTGTGTGTGGAGATACAACTGGCTCCTCGG</u>TGAC
TCTAGGATGCCTGGTCAAG AGATCT TCC

CDR1                        CDR2
<u>LPEFQVQLEQSGAELVRPGASVTVSCKAS</u>|GYTFTDYEMH|<u>WVKQTPVHGLEWIG</u>|AIDPETGGTAYNQKFKG|<u>ATLTADKSSSTAYM
ELRSLTSEESAVYYCTR</u>|PSSYDAMDY|<u>WGQGTSVTVSSAKTTAPSVYPLAPVCGDTTGSS</u><u>VTLGCLVKRSS</u>
          CDR3

B Spike492-1G10E4E2 kappa chain

<u>GG GAGCTC</u>
<u>GATATTGTGCTGACACAGTCTACACTCTCCCTGCCTGTCAGTCTTGGAGATCAAGCCTCCATCTCTTGCAGATCTAGTCAGAGCA
TTGTACATAGTAATGGAAACACCTATTTAGAATGGTACCTGCAGAAACCAGGCCAGTCTCCAAAGCTCCTGATCTACAAAGTTTC
CAACCGATTTTCTGGGGTCCCAGACAGGTTCAGTGGCAGTGGATCAGGGACAGATTTCACACTCAAGATCAGCAGAGTGGAGGCT
GAGGATCTGGGAATTTATTACTGCTTTCAAGGTTCACATGTTCCGTACACGTTCGGAGGGGGGACCAAGCTGGAAATAAAACGGG
CT</u>GATGCTGCACCAACTGTATCC GCATGC ACC

CDR1                      CDR2
<u>ELDIVLTQSTLSLPVSLGDQASISC</u>|RSSQSIVHSNGNTYLE|<u>WYLQKPGQSPKLLIY</u>|KVSNRFS|<u>GVPDRFSGSGSGTDFTLKISRV
EAEDLGIYYC</u>|FQGSHVPYT|<u>FGGGTKLEIKRA</u><u>DAAPTVSACT</u>
          CDR3

[Fig. 7]

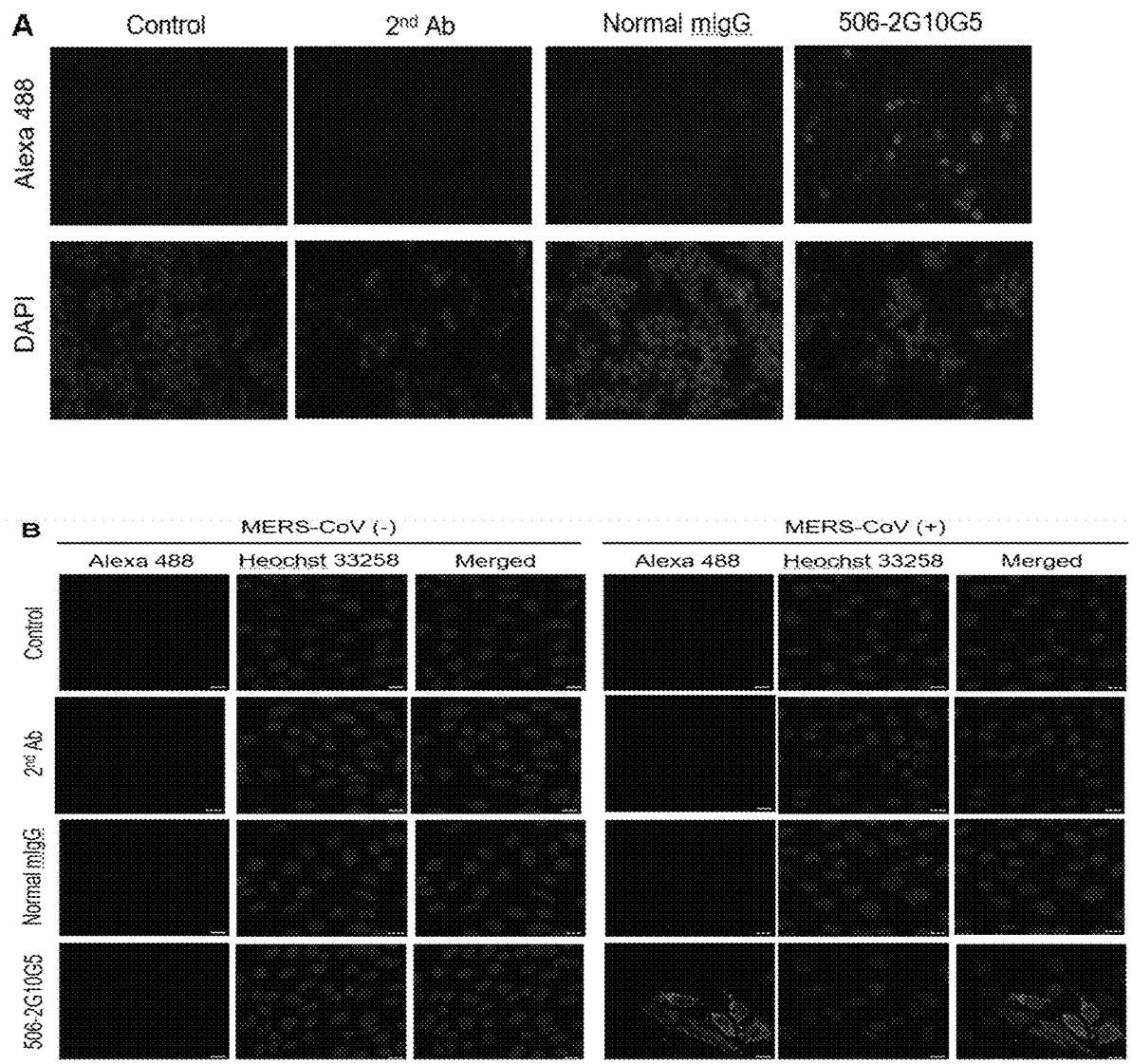
[Fig. 8]

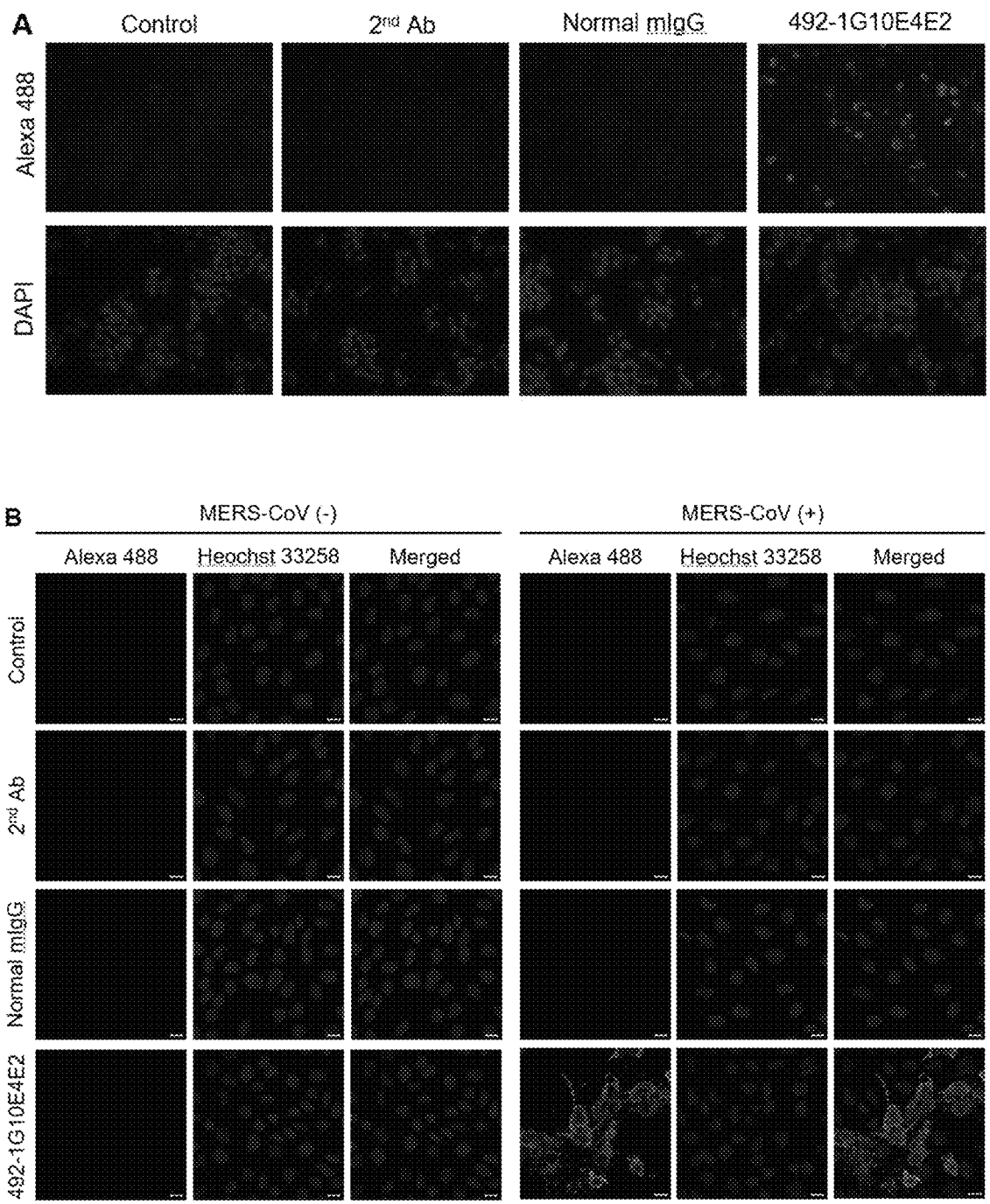
[Fig. 9]

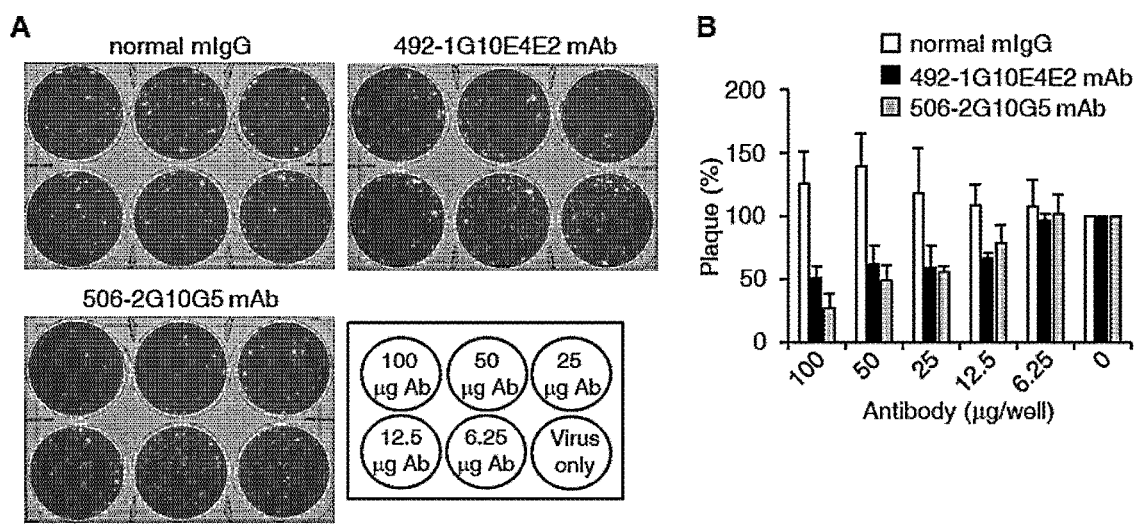
[Fig. 10]

MONOCLONAL ANTIBODY THAT BINDS A MERS-CORONAVIRUS

TECHNICAL FIELD

The present invention relates to a monoclonal antibody against MERS coronavirus S protein and use of the same.

REFERENCE TO AN ELECTRONIC SEQUENCING LISTING

The content of the electronic sequencing listing (OP19-0020HSUS_ST25.txt; Size: 10,781 bytes; and Date of Creation: Jun. 14, 2024), filed via Patent Center on Jun. 14, 2024, is herein incorporated by reference in its entirety.

BACKGROUND ART

Middle East respiratory syndrome coronavirus (ME RS-CoV, Middle East Respiratory Syndrome Coronavirus) is a virus that has been intensively developed in the Middle East since it was first discovered in Saudi Arabia in 2012. It is known as a virus similar to the virus (SARS-CoV, severe acute respiratory syndrome coronavirus).

MERS (Middle East Respiratory Syndrome) has a latent period of about 1 week, and mainly shows respiratory symptoms such as cough accompanied by fever, shortness of breath, shortness of breath, and phlegm. Digestive symptoms such as vomiting, abdominal pain, and diarrhea may also appear. However, unlike SARS, it is accompanied by acute renal failure. The fatality rate is 6 times higher than that of SARS. Depending on the age group, the mortality rate exceeds 50%. Until now, antiviral drugs for the treatment of the Middle East Respiratory Syndrome virus have not been developed, and treatment for symptoms is mainly performed.

Although no clear source of infection and path of infection have been identified, it has been reported that the possibility of infection is high through contact with camels in the Middle East and transmission through close contact between people is possible. MERS-CoV is a type of beta coronavirus among coronaviruses. The gene length varies, but corresponds to about 30 kb and has 11 open reading frames (ORFs). Structural proteins of MERS-CoV include S (spike), E (envelope), M (membrane) and NP (nucleocapsid) proteins.

The diagnosis of MERS-CoV is classified into gene diagnosis and antigen-antibody diagnosis. The standard diagnosis method currently recommended by WHO is for PCR or gene sequencing using a virus gene-specific primer from a nasal swap sample. The antibody diagnosis method of MERS-CoV is an antibody diagnosis ELISA (enzyme-linked immunosorbent assay, enzyme immunosorbent assay) method for NP antigen, and the antibody diagnosis kit developed by Euroimmun (Germany) is used to diagnose MERSCoV in camels. However, no product has been developed as a human antigen-antibody diagnostic kit yet.

Korean Patent No. 1593641 discloses 'An antibody recognizing Middle East Respiratory Syndrome coronavirus nucleocapsid and its use', and Korean Patent No. 0832870 discloses 'a monoclonal antibody against the SARS coronavirus nucleocapsid protein and its use is disclosed.

Prior Patent Literature

Korean Patent Publication No. 10-2016-0145813

DISCLOSURE

Technical Problem

An object of the present invention is to provide a novel monoclonal antibody specific for the S protein of MERS-CoV.

Another object of the present invention is to provide a method for producing a monoclonal antibody specific for the S protein of MERS-CoV.

Technical Solution

In order to achieve the above object, the present invention relates to a monoclonal antibody specifically recognizing a protein of MERS coronavirus (MERS-CoV) or a part of the protein, or a functional fragment of the monoclonal antibody, characterized in that that it comprises polypeptide sequence selected from the group consisting of the following polypeptide sequences:
  a heavy chain comprising a complementarity determining region 1 (CDR 1) amino acid sequence consisting of the sequence of SEQ ID NO: 1, a CDR2 consisting of the sequence of SEQ ID NO: 2 and a CDR 3 consisting of the sequence of SEQ ID NO: 3; and
  a light chain comprising CDR1 amino acid sequence consisting of the sequence of SEQ ID NO: 4, a CDR2 consisting of the sequence of SEQ ID NO: 5 and a CDR 3 consisting of the sequence of SEQ ID NO: 6.

According to an embodiment of the present invention, said functional fragment is preferable a single chain variable fragment (scFv); a Fab; a light chain or a heavy chain comprising the CDR region of the monoclonal antibody; or a variable domain comprising the CDR region of the monoclonal antibody, but is not limited thereto. In another embodiment of the present invention, the monoclonal antibody is preferably a heavy chain comprising a polypeptide sequence represented by SEQ ID NO: 7 and a light chain comprising a polypeptide sequence represented by SEQ ID NO: 8, but is not limited thereto.

In another embodiment of the present invention, the protein of the MERS coronavirus (MERS-CoV) is preferably an S protein, and a part of the S protein is more preferably a peptide sequence described in SEQ ID NO: 9, but limited thereto.

In addition, the present invention provides a monoclonal antibody that recognizes the peptide sequence represented by SEQ ID NO: 9 as an epitope.

In addition, the present invention provides a method for producing a monoclonal antibody that recognizes the MERS coronavirus by injecting the MERS coronavirus-derived epitope peptide and CpG-DNA complex co-encapsulated in the liposome into an animal.

In addition, the present invention provides a monoclonal antibody prepared by the method of the present invention.

Further, the present invention provides a composition for diagnosis of MERS coronavirus comprising a conjugate obtained by conjugating a labeling substance to the monoclonal antibody of the present invention.

In one embodiment of the present invention, the labeling material is preferably any one selected from the group consisting of enzymes, luciferases, magnetic particles, fluorescent materials, and radioactive isotopes, but is not limited thereto.

In addition, the present invention provides a method of providing information on whether a subject is infected with MERS coronavirus comprises the steps 1) contacting a sample with a monoclonal antibody of the present invention; and 2) detecting the antigen-antibody complex formed by contacting the monoclonal antibody with a sample.

In addition, the present invention provides a kit for diagnosis of MERS coronavirus comprising the monoclonal antibody of the present invention and a container.

In addition, the present invention provides a kit for diagnosis of MERS coronavirus comprising is the composition of the present invention and a container.

The present invention provides a method for detecting a MERS coronavirus comprising the step of detecting an antigen-antibody complex formed by contacting the monoclonal antibody with a sample.

In the present invention, the term "antigen-antibody complex" refers to a combination of the MERS-CoV S antigen in a sample and a monoclonal antibody or fragment thereof according to the present invention that recognizes it, and the antigen-antibody complex can be detected by any method selected from the group consisting of a colorimetric method, electrochemical method, fluorescence method, luminometry, particle counting method, visual assessment, and scintillation counting method. However, it is not necessarily limited to these method, and various applications and applications are possible.

In the present invention, various markers can be used for detecting the antigen-antibody complex. Specific examples may be selected from the group consisting of enzymes, fluorescent substances, ligands, luminescent substances, microparticles, and radioactive isotopes, but are not limited thereto.

Preferred enzymes used as detection markers include acetylcholinesterase, alkaline phosphatase, β-D-galactosidase, horseradish peroxidase, or β-lactamase. Preferred fluorescent substances include fluorescein, Eu3+, Eu3+ chelate or cryptate, preferred ligands include biotin derivatives, preferred luminescents include acridinium esters or isoluminol derivatives, preferred microparticles include colloidal gold or colored latex, Preferred radioactive isotopes include 57Co, 3H, 125I or 125I-Bolton Hunter's reagent, but are not limited thereto.

The method of detecting the antigen-antibody complex may preferably be detected using an enzyme immunosorbent method (ELISA), but is not limited thereto. Enzyme immunosorbent includes various ELISA methods, such as a direct ELISA using an antibody that recognizes an antigen attached to a solid support, an indirect ELISA using a labeled secondary antibody that recognizes the capture antibody in a complex of antibodies that recognize an antigen attached to a solid support, a direct sandwich ELISA using another labeled antibody that recognizes an antigen in a complex of an antibody and an antigen attached to a solid support, and an indirect sandwich ELISA using a labeled secondary antibody that recognizes this antibody after reacting with another antibody that recognizes an antigen in a complex of an antibody and an antigen attached to a solid support.

The monoclonal antibody or fragment thereof may have a detection label, and if it does not have a detection label, these monoclonal antibodies or fragments thereof can be captured, and can be identified by treatment with another antibody having a detection label.

In addition, the present invention provides a kit for detecting MERS coronavirus comprising the monoclonal antibody.

The detection kit of the present invention includes the monoclonal antibody, an antibody conjugated with a label that develops color by reacting with a substrate, and a color developing substrate. In the detection kit of the present invention, the monoclonal antibody may be provided in a state adsorbed on a substrate. PVDF film, plate, and slide may be used as the substrate, but are not limited thereto. HRP as a label and TMB as a color developing substrate are preferable, but are not limited thereto. In addition, the detection kit is one suitable for an analysis method. Or it may further include a composition, solution, or device having other components than that. Diagnosing MERS in humans using a monoclonal antibody specific to the MERS coronavirus S antigen prepared according to the manufacturing method of the present invention. A detection kit is provided for the following. As the final detection method of the detection kit, immunochromatography, rapid diagnostics, enzyme immunosorbent (ELISA), or western blot may be used, but is not limited thereto. Preferably, the detection method used in the detection kit of the present invention may be an immunochromatography method and an enzyme immunosorbent method. The kit for detecting MERS coronavirus using the immunochromatography method includes: a sample injection unit for injecting a sample; a coupling part including a gold condensate to which a monoclonal antibody capable of specifically binding to MERS coronavirus S protein located at a point spaced apart from the sample injection part; a test line in which a monoclonal antibody capable of specifically binding to the MERS coronavirus S protein is fixed at a position spaced apart from the binding portion at a predetermined interval; and a control line to which anti-mouse IgG is fixed is preferably provided sequentially, but is not limited thereto.

In one embodiment of the present invention, the detection kit includes a sample injection unit through which a sample can be injected by bonding a pad made of glass fiber, cotton, or cellulose to a strip-shaped nitrocellulose membrane, and a condensation pad in which a colloidal gold-MERS coronavirus antibody condensed complex is dried while maintaining a certain distance from the sample injection part, and an immuno-strips sequentially provided with a test line on which another antibody capable of detecting the same antigen as the MERS coronavirus antibody is fixed and a control line on which a secondary antibody capable of detecting a monoclonal antibody present in the condensation pad is fixed.

The immunochromatographic diagnostic method is stable and can be stored for a long time by using a kit to which the dry composition for detecting MERS coronavirus is applied.

If a sample suspected of containing the MERS coronavirus is added to the MERS coronavirus detection kit and a red purple band appears on the test line and the control line of the test strip, the MERS coronavirus infection is determined as positive, and If red purple bands appear only the control line, MERS coronavirus infection can be determined as negative.

In addition, by applying the other respiratory virus virus in the cross reaction test, reading that the test result is negative, it is possible to confirm how much the test does not have cross-reaction with the other respiratory virus.

In the case of a kit using the enzyme immune antibody method, a sample collected from a suspected MERS patient is reacted to each well of a plate coated with a monoclonal antibody of the present invention, and HRP (Horseradish peroxidase)-conjugated MERS-CoV S antigen-specific monoclonal antibody After adding, TMB (3,3',5,5'-tetramethylbenzidine) substrate solution is treated in each well to measure the color reaction by absorbance. Preferably, the detection kit of the present invention uses a specific monoclonal antibody for differential diagnosis of MERS from human corona virus, and a recombinant S antigen may be additionally included to enable a positive control and quantitative analysis.

The diagnostic composition according to the present invention may contain a monoclonal antibody of the present invention and a reagent used for immunological analysis. Reagents used for immunological analysis include suitable carriers used in all known quantitative assay methods based on antigen-antibody binding, labels capable of generating detectable signals, solubilizers, and detergents. Examples of the quantitative analysis method include, but are not limited to, immunoblotting, immunoprecipitation, enzyme immunoassay, protein chip, rapid assay, and microarray method.

Suitable carriers in the above include, but are not limited to, a soluble carrier, such as any one of physiologically acceptable buffers known in the art (e.g., PBS) or an insoluble carrier, such as polystyrene, polyethylene, polypropylene, polyester, polyacrylonitrile, fluorocarbon resin, crosslinked dextran, polysaccharide, glass, metal, agarose, and combinations thereof.

As a label capable of generating a detectable signal, an enzyme, a fluorescent substance, a luminescent substance, and a radioactive substance may be used. Enzymes include peroxidase, alkaline phosphatase, β-D-galactosidase, glucose oxidase, maleate dehydrogenase, glucose-6-phosphate dehydrogenase, and invertase. Fluorescein isothiocyanate, phycobilin protein, rhodamine, phycoerythrin, phycocyanin and orthophthalic aldehyde may be used as fluorescent materials. As a light-emitting material, isolumino, lucigenin, etc. may be used, and as a radioactive material, $^{131}I$, $^{14}C$, $^{3}H$, and the like may be used. However, in addition to those exemplified above, whichever that can be used in an immunological assay may be used.

Functional antibody fragments of the present invention include light chain, heavy chain, variable region, Fab, Fab', F (ab')2, scFv, Diabody, Tribody, dsFv, and peptides containing CDRs.

Fab is a fragment obtained by treating IgG with the protease papain (cut to the 224th amino acid residue of the heavy chain), about half of the N-terminal side of the heavy chain and the whole light chain are bound by disulfide bonds (S—S bonds). It is an antibody fragment with antigen-binding activity having 50,000 Molecular weight. The Fab of the present invention can be obtained by treating the antibody of the present invention with the protease papain. Alternatively, the DNA encoding the Fab of the antibody is inserted into a prokaryotic expression vector or an expression vector for eukaryotes, and the vector is introduced into a prokaryote or eukaryote to express it to prepare a Fab.

$F(ab')_2$ is a fragment obtained by treating IgG with the protease pepsin (cut to the 234th amino acid residue in the heavy chain) and it is an antibody fragment having an antigen-binding activity of about 100,000 M.W. that Fab bound through the S—S bond of the hinge region.

$F(ab')_2$ of the present invention can be obtained by treating the antibody of the present invention with the protease pepsin. Alternatively, it can be produced by preparing the following Fab' with thioether binding or S—S binding. Fab' is an antibody fragment having an antigen-binding activity of about 50,000 molecular weight by cleaving the S—S bond of the hinge region of F $(ab')_2$.

scFv is a VH-P-VL or VL-P-VH polypeptide in which one VH and one VL are linked using a suitable peptide linker (P) of 12 or more residues and is an antibody fragment having antigen-binding activity.

The scFv of the present invention obtains cDNA encoding VH and VL of the antibody of the present invention, constructs a DNA encoding scFv, and inserts the DNA into an expression vector for prokaryote or an expression vector for eukaryote to obtain the expression vector. It can be produced by expression by introduction into prokaryotes or eukaryotes.

Diabody is an antibody fragment in which scFvs having the same or different antigen-binding specificities form a dimer and is an antibody fragment having a bivalent antigen-binding activity for the same antigen or a bispecific antigen-binding activity for different antigens.

Diabody of the present invention, for example, obtains cDNA encoding VH and VL of the antibody of the present invention, constructs a DNA encoding scFv having a polypeptide linker of 3 to 15 residues, and expresses the DNA for prokaryote By inserting into a vector or an expression vector for eukaryotes, the expression vector can be introduced into a prokaryote or eukaryote to express a Diabody.

In addition, when the linker P length is 3-10, a tribody is formed and may be included as a tribody.

dsFv refers to a polypeptide obtained by substituting a cysteine residue for one of the amino acid residues of VH and VL, which is bonded via an S—S bond between the cysteine residues. Amino acid residues substituted with cysteine residues can be selected based on prediction of the conformational structure of an antibody according to the method described by Reiter et al. (Protein Engineering, 7, 697 (1994)). Further, the present invention provides a composition for treating MERS coronavirus infection, comprising the monoclonal antibody of the present invention or a functional fragment thereof as an active ingredient.

Pharmaceutically acceptable carriers included in the pharmaceutical composition of the present invention are those commonly used in formulation, lactose, dextrose, sucrose, sorbitol, mannitol, starch, gum acacia, calcium phosphate, alginate, gelatin, Calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, etc. The pharmaceutical composition of the present invention may further include lubricants, wetting agents, sweetening agents, flavoring agents, emulsifying agents, suspending agents, preservatives, etc. in addition to the above components. Suitable pharmaceutically acceptable carriers and formulations are described in detail in Remington's Pharmaceutical Sciences (19th ed, 1995).

The pharmaceutical composition of the present invention can be administered orally or parenterally, preferably parenteral, and in the case of parenteral administration, it can be administered by intravenous injection, subcutaneous injection, intramuscular injection, intraperitoneal injection, transdermal administration, etc.

A suitable dosage of the pharmaceutical composition of the present invention can be formulated in various ways depending on factors such as formulation method, mode of administration, age, weight, sex, pathological condition, food, administration time, route of administration, excretion rate and response sensitivity. Meanwhile, the dosage of the pharmaceutical composition of the present invention is preferably 0.001-10,000 mg/kg (body weight) per day.

The pharmaceutical composition of the present invention is prepared in a unit dosage form by formulating using a pharmaceutically acceptable carrier and/or excipient according to a method that can be easily carried out by a person having ordinary knowledge in the art. Or it can be prepared by placing it in a multi-dose container. In this case, the formulation may be in the form of a solution, suspension, or emulsion in an oil or aqueous medium, or may be in the form of an extract, powder, granule, tablet or capsule, and may additionally include a dispersant or a stabilizer.

The present invention will be described below.

In this invention, we selected novel B cell epitope peptide sequences, Spike-492 and Spike-492 (L506F), from MERS-CoV S protein-RBD representative of South Korea and Saudi Arabia strains. The B cell epitope peptide sequence, Spike-492 (L506F), of MERS-CoV S protein-RBD encodes L506F substitution. Herein, we generated monoclonal antibodies, 506-2G10G5 and 492-1G10E4E2, specific against S protein of MERS-CoV S protein by immunizing mice with a complex of B cell epitope peptide and Lipoplex (O). Both monoclonal antibodies showed strong specific binding to S protein of MERS-CoV, however, 506-2G10G5 monoclonal antibody showed higher binding affinity to Spike-492 and Spike-492 (L506F) peptide when compared to 492-1G10E4E2. Moreover, data from indirect immunofluorescence assay and confocal assay confirmed the specificity of both monoclonal antibodies toward S protein. Importantly, 506-2G10G5 monoclonal antibody treatment effectively reduced the MERS-CoV infected plaque percentage in compared to normal mouse IgG and 492-1G10E4E2 treatment. Taken together, our data indicate the potential of 506-2G10G5 monoclonal antibody for diagnostic and therapeutic against emerging MERS-CoV infection.

Effects of the Invention

As can be seen through the present invention, the 506-2G10G5 monoclonal antibody of the present invention may be applied to diagnosis and treatment of MERS-CoV infection.

DESCRIPTION OF DRAWINGS

FIG. 1A-C. Production of B cell epitope-specific antibody. (A) Schematic representation of MERS-CoV S protein. S protein consists of S1 and S2 subunits. RBD, receptor binding domain: FP, fusion peptide: HR1 and HR2, heptad repeat region 1 and 2; TM, transmembrane: CP, cytoplasmic tail. (B) Selection of B cell epitope peptide sequence using the IEDB on the basis of epitope prediction, surface accessibility and antigenicity index wherein Spike-492 amino acid sequence is represented by SEQ ID NO: 9 and Spike-492 (L506F) amino acid sequence is represented by SEQ ID NO: 10. (C) ELISA analysis showing generation of MERS-CoV Spike-492- or Spike-492 (L506F)-specific antibodies using sera. Sera were isolated from BALB/c mice immunized with the complex of B cell epitope peptide (Spike-492 or Spike-492 (L506F)) and Lipoplex (O).

FIG. 2A-D. Screening of hybridoma clone producing anti-Spike-492 (L506F)-specific monoclonal antibody (506-2G10G5). (A, B) Three BALB/c mice were immunized i.p. with Spike-492 (L506F) peptide and MB-ODN 4531 (O) coencapsulated in a DOPE:CHEMS complex on four occasions at 10 day intervals. ELISA results from the initial screening (HAT medium) of a cell-fusion experiment using splenocytes of Spike-492 (L506F) peptide immunized mice. (C, D) Hybridoma clones were selected for the production of monoclonal antibody following subcloning by limiting dilution method in HT medium.

FIG. 3A-F. Screening of hybridoma clone producing anti-Spike-492-specific monoclonal antibody (492-1G10E4E2). (A, B) Three BALB/c mice were immunized i.p. with Spike-492 peptide and MB-ODN 4531 (O) coencapsulated in a DOPE:CHEMS complex on four occasions at 10 day intervals. ELISA results from the initial screening (HAT medium) of a cell-fusion experiment using splenocytes of Spike-492 peptide immunized mice. (C-F) Hybridoma clones were selected for the production of monoclonal antibody following subcloning by limiting dilution method in HT medium.

FIG. 4A-I. Purification and characterization of anti-MERS-CoV Spike-492 (L506F) epitope-specific monoclonal antibody. (A) The pristine-primed mice was injected with 506-2G10G5 clone and ascites was obtained. Subsequently, 506-2G10G5 monoclonal antibody was purified using Protein A agarose column chromatography and performed SDS-PAGE analysis. R, reducing condition: NR, non-reducing conditions. (B) Isotype of purified 506-2G10G5 monoclonal antibody was determined by ELISA. (C) The binding affinity of 506-2G10G5 monoclonal antibody to MERS-CoV Spike-492 (L506F) peptide was measured by ELISA and $EC_{50}$ value was evaluated with Sigma Plot program. (D-F) MERS-CoV-infected and non-infected Vero cells lysates were treated with PBS (−) or PNGase F (+). The lysates were immunoblotted with 506-2G10G5 monoclonal antibody (D). Lysates were subjected to western blotting with an anti-β actin antibody as control (E). Western blot analysis using 506-2G10G5 monoclonal antibody was performed following the immunoprecipitation of lysates with 506-2G10G5 monoclonal antibody (F). Lysates were subjected to western blotting with an anti-β actin antibody as control (G). (H, I) Cross-reactivity of the monoclonal antibodies. 96-well immunoplates coated with MERS-CoV Spike-492 (G) or Spike-492 (L506F) (H) peptides and incubated with either the 492-1G10E4E2 or 506-2G10G5 monoclonal antibody. The reactivity of 492-1G10E4E2 monoclonal antibody to Spike-492 (L506F) peptide and that of 506-2G10G5 monoclonal antibody to Spike-492 peptide was determined by ELISA assay.

FIG. 5A-F. Purification and characterization of anti-MERS-CoV Spike-492 epitope-specific monoclonal antibody. (A) The 492-1G10E4E2 monoclonal antibody from ascites was purified using Protein A agarose column chromatography and analyzed by SDS-PAGE. R, reducing condition: NR, non-reducing conditions. (B) Determination of 492-1G10E4E2 monoclonal antibody isotype by ELISA. (C) The binding of 492-1G10E4E2 monoclonal antibody to MERS-CoV Spike-492 peptide was measured by ELISA and $EC_{50}$ value was analyzed with Sigma Plot program. (D-F) MERS-CoV-infected and non-infected Vero cells lysates were treated with PBS (−) or PNGase F (+). The lysates were immunoblotted with 492-1G10E4E2 monoclonal antibody (D). Western blot analysis using 492-1G10E4E2 monoclonal antibody was performed following the immunoprecipitation of lysates with 492-1G10E4E2 monoclonal antibody (E). Lysates were subjected to western blotting with an anti-β actin antibody as control (F).

FIG. 6A-B. The cDNA sequences for variable domains of heavy and light chains isolated from the hybridoma cell clone 506-2G10G5. (A) Sequence of the heavy chain variable domain wherein the nucleic acid sequence of Spike506-2G10G5 heavy chain is represented by SEQ ID NO: 15 and its amino acid sequence is represented by SEQ ID NO:7. (B) Sequence of the light chain variable domain. Predicted amino acid sequences are indicated under the cDNA sequences wherein the nucleic acid sequence of Spike506-2G10G5 kappa chain is represented by SEQ ID NO:16 and its amino acid sequence is represented by SEQ ID NO:8.

FIG. 7A-B. The cDNA sequences for variable domains of heavy and light chains isolated from the hybridoma cell clone 492-1G10E4E2. (A) Sequence of the heavy chain variable domain wherein the nucleic acid sequence of Spike492-1G10E4E2 heavy chain is represented by SEQ ID NO: 17 and its amino acid sequence is represented by SEQ ID NO: 18. (B) Sequence of the light chain variable domain. Predicted amino acid sequences are indicated under the cDNA sequences wherein the nucleic acid sequence of Spike492-1G10E4E2 kappa chain is represented by SEQ ID NO: 19 and its amino acid sequence is represented by SEQ ID NO:20.

FIG. 8A-B. Immunofluorescence assay and confocal microscopy for the detection of MERS-CoV-infected cells with Spike-492 (L506F) monoclonal antibody. (A) Indirect immunofluorescence assay. Mixture of MERS-CoV-infected and non-infected Vero cells were stained with 506-2G10G5 monoclonal antibody or normal mouse IgG, followed by incubation with Alexa488-conjugated goat anti-mouse IgG antibody (green). Cells were counterstained with Hoechst 33258 for nuclear staining (blue). Images were taken using fluorescence microscope. (B) Confocal microscopy. Vero cells were infected with MERS-CoV for 2 days. The cells were stained with 506-2G10G5 monoclonal antibody or normal mouse IgG and then incubated with Alexa488-conjugated goat anti-mouse IgG antibody (green). Nuclei were stained using Hoechst 33258 (blue). Scale bar, 10 μm.

FIG. 9A-B. Immunofluorescence assay and confocal microscopy for the detection of MERS-CoV-infected cells with 492-1G10E4E2 monoclonal antibody. (A) Indirect immunofluorescence assay. Mixture of MERS-CoV-infected and non-infected Vero cells were stained with 492-1G10E4E2 monoclonal antibody or normal mouse IgG, followed by incubation with Alexa488-conjugated goat anti-mouse IgG antibody (green). Cells were counterstained with Hoechst 33258 for nuclear staining (blue). Images were taken using fluorescence microscope. (B) Confocal microscopy. Vero cells were infected with MERS-CoV for 2 days. The cells were stained with 492-1G10E4E2 monoclonal antibody or normal mouse IgG and then incubated with Alexa488-conjugated goat anti-mouse IgG antibody (green). Nuclei were stained using Hoechst 33258 (blue). Scale bar, 10 μm.

FIG. 10A-B. Inhibition of MERS-CoV infection by 506-2G10G5 and 492-1G10E4E2 monoclonal antibody. MERS-Co Virus were pre-incubated with two fold serial diluted normal mouse IgG, 492-1G10E4E2 monoclonal antibody or 506-2G10G5 for 30 min at 37° C. The virus-antibody mixture was added to Vero cells and incubated for 1 h. After incubation medium was replaced with DMEM/F12 containing 0.6% oxoid agar. The plaques were stained with crystal violet following 4 days after infection. (A) A representative picture showing plaque reduction assay. (B) Quatification of plaque reduction assay against MERS-CoV after treatment with 100 μg/well to 0 μg/well of normal mouse IgG or 492-1G10E4E2 or 506-2G10G5 monoclonal antibody.

MODE FOR INVENTION

Hereinafter, the embodiments of the present invention will be described in detail with reference to the attached exemplary drawings, as such an example, a person skilled in the art to which the present invention pertains may be implemented in various different forms, it is not limited to the embodiment described here.

Vero cells, the African green monkey kidney cells, were obtained from the American Type Culture Collection (ATCC, Manassas, VA, USA). Dulbecco's modified Eagle's medium (DMEM) purchased from Life Technologies (Thermo Fisher Scientific, Waltham, MA, USA) with supplementation of 10% fetal bovine serum (FBS, Thermo Fisher Scientific), 25 mM HEPES, 100 U/ml penicillin and 100 μg/ml streptomycin was used in culture of Vero cells. The cells were incubated in an atmosphere of 5% $CO_2$ and 95% air at 37° C. MERS-CoV/KOR/KNIH/002_05_2015 was obtained from the Korea Centers for Disease Control and Prevention (Permission No. 1-001-MER-IS-2015001).

Example 1: B Cell Epitope Peptides Preparation

The selection, analysis and synthesis of a B cell epitopes peptide of MERS-CoV S protein was performed as described previously (Park B K, Lee S I, Bae J-Y et al (2018) Int J Pept Res Ther https://doi.org/10.1007/s10989-018-9731-8). The B cell epitope peptide sequences for the S protein of MERS-CoV are selected as Spike-492 ($^{492}$TKPLKYSYINKCSRLLSDDRTEVPQ$^{516}$; SEQ ID NO:9) from MERS-CV strain (MERS-CoV/KOR/KNIH/002_05_2015 (GI: 829021049)) and Spike-492 (L506F) (492TKPLKYSYINKCSRFLSDDRTEVPQ$^{516}$; SEQ ID NO: 10) from MERS-CV strain (Spike glycoprotein universal sequence (GI: 510785803)), and synthesized with an automated peptide synthesizer (Peptron III-R24, Peptron, Daejeon, Korea). The complex of B cell epitope peptide and CpG-DNA (MB-ODN 4531 (O)) co-encapsulated in the DOPE:CHEMS (named as Lipoplex (O)) were prepared.

Example 2: Mice Immunization 4-week-old BALB/c (H-2b) female mice were purchased from Nara-Biotec (Seoul, Korea). The mice were maintained at animal facility Hallym University under specific pathogen-free conditions. All the experiments involving animals were carried out with approval from the Institutional Animal Care and Use Committee of Hallym University (Hallym2016-51). The mice were intraperitoneally immunized thrice at 10-day intervals with 200 μl of Spike-492 peptide (50 μg) or Spike-492 (L506F) peptide (50 μg) and Lipoplex (O) complex.

Example 3: Production of Mouse Anti-MERS-CoV S Protein Monoclonal Antibody

In accordance with standard hybridoma technique, hybridoma cells were selected to produce anti-Spike-492-specific monoclonal antibody (492-1G10E4E2) and anti-Spike-492 (L506F)-specific monoclonal antibody (506-2G10G5) [Wu G, Kim D, Kim J N et al (2018) Theranostics 8, 78-91; W. M. Yokoyama, M. Christensen, G. D. Santos, et al., Curr. Protoc. Immunol., Chapter 2 (2006), Unit 2.5]. On three occasions at 10 day intervals, BALB/c mice were injected i.p. with MERS-Spike-492 peptide (50 μg) (or Spike-492 (L506F) peptide) and MB-ODN 4531 (O) (50 μg) encapsulated in DOPE:CHEMS complex. The spleens from the immunized mice were used for fusion in accordance with standard hybridoma technique. Hybridoma clone in HAT medium and HT medium were selected by a standard limiting dilution protocol to obtain clonal cell population. To obtain the ascites, the selected hybridoma clones (492-1G10E4E2 clone and 506-2G10G5) were injected in peritoneal cavity of BALB/c mouse. Anti-Spike-492-specific monoclonal antibody (492-1G10E4E2) and anti-Spike-492 (L506F)-specific monoclonal antibody (506-2G10G5) were purified from the ascites fluid by protein-A column chromatography. To determine the isotype of the monoclonal antibodies, an isotyping kit (Southern Biotechnology Associates Inc, Birmingham, USA) was used.

Example 4: ELISA Assay

To measure the epitope peptide-specific antibody titer, 96-well immunoplates (Thermo Fisher Scientific) were coated with 5 μg/well of MERS-CoV Spike-492 or Spike-492 (L506F) peptides and incubated at 4° C. overnight, washed with PBST (PBS supplemented with 0.05% Tween-20) and blocked with PBST containing 1% bovine serum albumin (BSA). The mice sera obtained by retro orbital bleeding were serially diluted at 1:3 ratio and added to wells of each plate followed by incubation for 2 h at room temperature. Horseraddish peroxidase (HRP)-conjugated goat anti-mouse IgG (Jackson ImmunoResearch laboratories, West Grove, PA, USA) was used as secondary antibody for 1 h. After washing with PBST, tetramethylbenidine (TMB) peroxidase substrate (KPL, SeraCare, Milford, MA, USA) was treated and reactions were stopped with TMB-stop solution (KPL). The absorbance was read using Spectra Max 250 microplate reader (Molecular Devices, San Jose, CA, USA) at 450 nm. For the identification of isotype of the monoclonal antibody, HRP-conjugated anti-mouse IgG (each isotype) antibody (Southern Biotech, Birmingham, AL, USA) was used. For detection of cross-reactivity, 96-well immunoplates were coated with MERS-CoV Spike-492 or Spike-492 (L506F) peptides as described above. The coated wells were incubated with either the 492-1G10E4E2 monoclonal antibody or 506-2G10G5 monoclonal antibody for 2 h before the secondary antibody incubation.

Example 5: Affinity Constant Measurement by ELISA

To measure the binding affinity of the Anti-Spike-492-specific monoclonal antibody (492-1G10E4E2) and anti-Spike-492 (L506F)-specific monoclonal antibody (506-2G10G5), 5 μg/well of Spike-492 and Spike-492 (L506F) epitope peptide was coated on 96-well immunoplates and then blocked with PBST containing 1% BSA. The monoclonal antibody was added to the each plate with serial 1:5 dilutions in PBST and then incubated for 2 h at room temperature. After washing with PBST, anti-IgG antibody conjugated with horseradish peroxidase was added to the each plate. The amounts of antibody in plates were determined by developing with tetramethylbenzidine (TMB) peroxidase substrate (KPL, SeraCare, Milford, MA, USA). The absorbance was evaluated with the Spectra Max 250 microplate reader (Molecular Devices, San Jose, CA, USA) at 405 nm and the calculated with the SigmaPlot program to determine the EC50 value.

Example 6: Western Blotting and Immunoprecipitation

MERS-CoV-infected Vero cell lysates were run on SDS-PAGE and subsequently transferred onto a nitrocellulose membrane. The membranes were blocked with 3% BSA in PBST. Then, the membrane were incubated with MERS-CoV Spike-492 monoclonal antibody or Spike-492 (L506F) monoclonal antibody, washed with PBST and treated with HRP-conjugated goat anti-mouse IgG antibody. The membrane was detected with chemiluminescence solution and picturized with ChemiDoc (Bio-Rad, Herculed, California, USA). For immunoprecipitation, virus infected-Vero cell lysates were incubated with MERS-CoV Spike-492 monoclonal antibody or Spike-492 (L506F) monoclonal antibody overnight at 4° C. and proteins (S protein of MERS-CoV) were precipitated with Protein-A beads (Repligen, Waltham, MA, USA) for 1 h. The immunoprecipitated proteins were analyzed using MERS-CoV Spike-492 monoclonal antibody or Spike-492 (L506F) monoclonal antibody by western blotting.

Example 7: Deglycosylation Assay

MERS-CoV-infected and non-infected Vero cells were lysed with lysis buffer (0.5% SDS and 1% B-mercaptoethanol) and boiled at 100° C. for 10 min. The lysates were then subjected to peptide-N-glycosidase F (PNGase F) (Elpis Biotech, Daejeon, Korea) treatment at 37° C. for 2 h and boiled at 100° C. for 10 min. After the digestions, the samples were detected with MERS-CoV Spike-492 monoclonal antibody or Spike-492 (L506F) monoclonal antibody by western blot. For immunoprecipitation, the PNGase F digested samples were incubated with MERS-CoV Spike-492 monoclonal antibody or Spike-492 (L506F) monoclonal antibody overnight at 4° C. followed by western blot analysis with MERS-CoV Spike-492 monoclonal antibody or Spike-492 (L506F) monoclonal antibody.

Example 8: Cloning of the Variable Heavy and Light Domains of Anti-MERS CoV S Protein Monoclonal Antibody Hybridoma clones (492-1G10E4E2 clone and 506-2G10G5) producing Anti-Spike-492 peptide-specific monoclonal antibody (492-1G10E4E2) and anti-Spike-492 (L506F) peptide-specific monoclonal antibody (506-2G10G5) were cultured and isotyped using a mouse monoclonal antibody isotyping kit (Dipstick format, Bibco BRL or Roche, Mannheim, Germany). Total RNAs were extracted from hybridoma cells (492-1G10E4E2 clone and 506-2G10G5) with an RNeasy Mini Kit (Qiagen), and the cDNAs were generated. To clone the sequences for the variable heavy and light domains ($V_H$ and $V_L$) of anti-Spike-492 peptide-specific monoclonal antibody (492-1G10E4E2), the resultant cDNAs were amplified using Vent polymerase (NEB) with the following primer sets. For heavy chain primers, IGG2A (5'-GGA AGA TCT CTT GAC CAG GCA TCC TAG AGT CA-3"SEQ ID NO:11) and 5'MH2 (5'-CTT CCG GAA TTC SAR GTN MAG CTG SAG SAG TCW GG-3"SEQ ID NO:12) were used. For kappa chain primers, 3'Kc (5'-GGT GCA TGC GGA TAC AGT TGG TGC AGC ATC-3"SEQ ID NO:13) and 5'Mk (5'-GG GAG CTC GAY ATT GTG MTS ACM CAR WCT MCA-3"SEQ ID NO:14) were used. To clone the sequences for the variable heavy and light domains ($V_H$ and $V_L$) of anti-Spike-492 (L506F) peptide-specific monoclonal antibody (506-2G10G5), the resultant cDNAs were amplified using Vent polymerase (NEB) with the following primer sets. For heavy chain primers, IGG1 (5'-GGA AGA TCT ATA GAC AGA TGG GGG TGT CGT TTT GGC-3"SEQ ID NO:11) and 5'MH2 (5'-CTT CCG GAA TTC SAR GTN MAG CTG SAG SAG TCW GG-3"SEQ ID NO:12) were used. For kappa chain primers, 3'Kc (5'-GGT GCA TGC GGA TAC AGT TGG TGC AGC ATC-3"SEQ ID NO: 13) and 5'Mk (5'-GG GAG CTC GAY ATT GTG MTS ACM CAR WCT MCA-3"SEQ ID NO:14) were used. The standard PCR reaction was performed for 25 cycles. The PCR products were directly ligated into the pGEM-T easy vector (Promega). Cloned mouse Ig inserts were analyzed by DNA sequencing.

Example 9: Indirect Immunofluorescence Assay and Confocal Images

For analysis of indirect immunofluorescence assay, mixture of MERS-CoV-infected and non-infected Vero cells at the ratio of 3:1 were seeded onto slide glasses. The cells were then fixed with acetone and incubated with normal mouse IgG or MERS-CoV Spike-492 monoclonal antibody at 37° C. for 2 h. The samples were further incubated with Alexa Flour 488-conjugated goat anti-mouse IgG antibody (Thermo Fisher Scientific, Waltham, MA, USA). Finally, the samples were mounted and analyzed using fluorescence microscope (1×70, Olympus, Tokyo, Japan) (30, 31). To visualize confocal microcopy, Vero cells ($5\times10^4$) were seeded onto cover glass in 12 well plate and infected with MERS-CoV (0.1 MOI). After two days, the infected cells were fixed with 4% paraformaldehyde and subsequently blocked with 1% BSA and 0.1% triton X-100 in PBS. The slides were incubated in presence of MERS-CoV Spike-492 monoclonal antibody for 2 h, washed and then incubated with Alexa Flour 488-conjugated goat anti-mouse IgG antibody for 1 h. Hoechst 33258 (Thermo Fisher Scientific) was utilized to stain nuclei. The slides were examined by Carl Zeiss LSM710 (Carl Zeiss, Oberkochen, DE).

Example 10: Plaque Reduction Assay $6\times10^5$ Vero cells/well were plated on six-well plates (Thermo Fisher Scientific) and cultured for 12 h. Prior to infection, MERS-CoVirus were pre-incubated with two fold serial diluted normal mouse IgG, 492-1G10E4E2 monoclonal antibody or 506-2G10G5 for 30 min at 37° C. The virus-antibody mixture was added to Vero cells with 500 µl of PBS. After 1 h incubation, supernatant was removed and 3 ml of DMEM/F12 medium (Thermo Fisher Scientific) containing 0.6% oxoid agar were added. The plaques formed in each wells were stained with crystal violet following 4 days after infection. The plaques were counted and the percentage was calculated.

Analysis of B Cell Epitope and Production of Antibody Targeting S Protein Epitope of MERS-CoV B cell epitope identification and selection is one of the important considerations in epitope-based antibody production. Hence, the explicit B cell epitope amino acid sequence of MERS-CoV S protein was predicted utilizing Immune Epitope Database and Analysis Resources (IEDB) tool on the basis of epitope prediction, surface accessibility and antigenicity scale. Since RBD domain within the S protein are responsible for binding to host, Spike-492 and Spike-492 (L506F) peptide sequences with 492-516 amino acids within the RBD domain of MERS-CoV S protein was selected and synthesized (FIGS. 1A and B). For the determination of the efficiency as a B cell epitope, each peptides and Lipoplex (O) complex was formulated and then immunized into the BALB/c mice. In order to screen the antibody titers, ELISA was done from the serum of immunized mice. Both of the peptides were able to induce production of the peptide-specific IgGs (FIG. 1C). Thus, immunogenic epitope peptide were successfully designed and produced.

Production of Monoclonal Antibody Specific to Spike-492 (L506F) or Spike-492 Epitope of MERS-CoV To produce MERS-CoV S protein epitope-specific monoclonal antibody, splenocytes were collected from a complex of MERS-CoV Spike-492 epitope peptide (or Spike-492 (L506F) epitope peptide) and CpG-DNA co-encapsulated in liposome (DOPE;CHEMS)-immunized mice. The mouse splenocytes were fused with SP2/0, and Spike-492 (L506F) epitope peptide-specific antibody producing 506-2G10G5 clone was selected by HAT and HT supplements (FIG. 2). The mouse splenocytes were fused with SP2/0, and Spike-492 epitope peptide-specific antibody producing 492-1G10E4E2 clone was selected by HAT and HT supplements (FIG. 3).

Characterization of Monoclonal Antibody Specific to Spike-492 (L506F) or Spike-492 Epitope of MERS-CoV To obtain monoclonal antibody in large scale, 506-2G10G5 clone or 492-1G10E4E2 clone was injected into mouse peritoneal cavity for production of ascites. Ascites fluid were collected from mice injected with 506-2G10G5 clone or 492-1G10E4E2 clone and purified (FIG. 4A and FIG. 5A). Next, isotype classification of 506-2G10G5 or 492-1G10E4E2 monoclonal antibody was performed using ELISA and found to be IgG1 and IgG2a, respectively (FIG. 4B and FIG. 5B). The binding affinity of the monoclonal antibody targeting the Spike-492 (L506F) peptide or Spike-492 was determined with ELISA and an EC50 value of the monoclonal antibody 506-2G10G5 and 492-1G10E4E2 was found to have 178 pm and 3.3 nM, respectively (FIG. 4C and FIG. 5C).

Detection of MERS-CoV S Protein by the Monoclonal Antibody Specific to Spike-492 (L506F) or Spike-492 Epitope of MERS-CoV To further characterize the monoclonal antibody 506-2G10G5 or 492-1G10E4E2 recognizes S protein of MERS-CoV, western blotting and immunoprecipitation with MERS-CoV infected and non-infected Vero cells was performed. Western blotting results (FIG. 4D, FIG. 5D) showed that both monoclonal antibodies detected band specific to S protein in MERS-CoV-infected Vero cells but no band was observed in non-infected Vero cells. Treatment with peptide-N-glycosidase (PNGase F) resulted in the reduction of apparent molecular weight of S protein band in comparison to untreated sample (FIG. 4D and FIG. 5D) suggesting that both monoclonal antibodies could recognize S protein in its glycosylated and de-glycosylated form. Furthermore, immunoprecipitation was done to evaluate if the monoclonal antibodies could recognize the S protein in its native form. Here, we found that both monoclonal antibodies immunoprecipitated the native form of S protein from MERS-CoV-infected Vero cells lysates (FIG. 4F and FIG. 5E). To further determine the cross-reactivity of 506-2G10G5 and 492-1G10E4E2 monoclonal antibodies with each corresponding epitope, ELISA was performed. 506-2G10G5 monoclonal antibody showed remarkable cross-reactivity to Spike-492 peptides than shown by 492-1G10E4E2 monoclonal antibody to Spike-492 (L506F) (FIGS. 4H and I). Therefore, both the antibodies displayed specific binding to S protein of MERS-CoV.

Cloning of the Variable Domains of Anti-Spike-492 (L506F) Peptide-Specific and Anti-Spike-492 Peptide-Specific Monoclonal Antibody The cDNA sequences encoding the variable domains of heavy and light chains ($V_H$ and $V_L$) were cloned from hybridoma cells (506-2G10G5) producing anti-Spike-492 (L506F) peptide-specific monoclonal antibody using common heavy and light chain primers. The sequences confirmed by DNA sequencing are shown in FIG. 6. The cDNA sequences encoding the variable domains of heavy and light chains ($V_H$ and $V_L$) were cloned from hybridoma cells (492-1G10E4E2) producing anti-Spike-492 peptide-specific monoclonal antibody using common heavy and light chain primers. The sequences confirmed by DNA sequencing are shown in FIG. 7. The sequences were analyzed for homology to known sequences by protein BLAST program. The cDNAs encoding variable domains of 506-2G10G5 and 492-1G10E4E2 heavy and light chains exhibited about 80~95% and 93~98% homology with the sequences of reported immunoglobulin variable heavy and light domains, respectively.

Reactivity of 506-2G10G5 or 492-1G10E4E2 Monoclonal Antibody to S Protein in the MERS-CoV-Infected Cells We further analyzed breadth of reactivity of 506-2G10G5 or 492-1G10E4E2 monoclonal antibodies with indirect immunofluorescence assay (IFA). Fluorescence microscopy displayed the strong fluorescence signal in the virus infected cells incubated with both monoclonal antibodies, whereas no fluorescence was observed when with normal mouse IgG (FIG. 8A and FIG. 9A). To further substantiate the specificity of both monoclonal antibodies to S protein of MERS-CoV, confocal microscopy was performed. MERS-CoV-infected or non-infected Vero cells were stained with normal mouse IgG or 506-2G10G5 or 492-1G10E4E2 monoclonal antibody. Images of confocal microscopy clearly showed the fluorescence signal within the cytosolic region of the MERS-CoV infected cells stained with 506-2G10G5 or 492-1G10E4E2 monoclonal antibody. No staining was observed in cells incubated with normal mouse IgG (FIG. 8B and FIG. 9B). These results demonstrated the specificity of both monoclonal antibodies in efficient detection of S protein of MERS-CoV in MERS-CoV-infected cells.

506-2G10G5 Monoclonal Antibody Inhibited MERS-CoV Infection in Vero Cells

We investigated the inhibitory activities of both the monoclonal antibodies against MERS-CoV in plaque reduction assay. In this assay, both monoclonal antibodies inhibited plaque formation when compared to normal mouse IgG in concentration dependent manner. However, better inhibition of plaque formation was observed when treated with 506-2G10G5 monoclonal antibody in comparison to 492-1G10E4E2 monoclonal antibody in concentration dependent manner (FIGS. 10A and B). Thus, the results demonstrated the efficacy of 506-2G10G5 monoclonal antibody, signifying its potential therapeutic applications against MERS-CoV infection.

---

The invention claimed is:

1. A monoclonal antibody that specifically binds a MERS coronavirus (MERS-CoV) and to the amino acid sequence of SEQ ID NO: 10, said antibody comprising a heavy chain variable domain consisting of an amino acid sequence of SEQ ID NO: 7 and a light chain variable domain consisting of an amino sequence of SEQ ID NO: 8, wherein the antibody comprises 6 CDRs with the amino acid sequences of SEQ ID NO: 1-6.

2. A MERS coronavirus diagnosis kit comprises the monoclonal antibody of claim 1 and a container.

* * * * *

SEQUENCE LISTING

```
<160> NUMBER OF SEQ ID NOS: 20

<210> SEQ ID NO 1
<211> LENGTH: 10
<212> TYPE: PRT
<213> ORGANISM: Artificial Sequence
<220> FEATURE:
<223> OTHER INFORMATION: CDR1 of VH

<400> SEQUENCE: 1

Gly Phe Thr Phe Ser Gly Phe Trp Met Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR2 of VH

<400> SEQUENCE: 2

Asp Ile Asn Ser Asp Gly Ser Ile Ile Asn Tyr Ala Pro Ser Ile Lys
1               5                   10                  15

Asp

<210> SEQ ID NO 3
<211> LENGTH: 8
<212> TYPE: PRT
<213> ORGANISM: Artificial Sequence
<220> FEATURE:
<223> OTHER INFORMATION: CDR3 of VH

<400> SEQUENCE: 3

Tyr Tyr Asp Ser Trp Phe Ala Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: CDR1 of VL

<400> SEQUENCE: 4

Arg Ser Ser Gln Ser Ile Val His Ser Asn Gly Asn Thr Tyr Leu Glu
```

-continued

<210> SEQ ID NO 5
<211> LENGTH: 7
<212> TYPE: PRT
<213> ORGANISM: Artificial Sequence
<220> FEATURE:
<223> OTHER INFORMATION: CDR2 of VL

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR3 of VL

<400> SEQUENCE: 6

Phe Gln Gly Ser His Val Pro Arg Thr
1               5

<210> SEQ ID NO 7
<211> LENGTH: 133
<212> TYPE: PRT
<213> ORGANISM: Artificial Sequence
<220> FEATURE:
<223> OTHER INFORMATION: Spike506-2G10G5 Heavy chain

<400> SEQUENCE: 7

Leu Pro Glu Phe Gln Val Lys Leu Gln Glu Ser Gly Gly Gly Leu Val
1               5                   10                  15

Gln Pro Gly Gly Ser Arg Gly Leu Ser Cys Glu Gly Ser Gly Phe Thr
            20                  25                  30

Phe Ser Gly Phe Trp Met Ser Trp Val Arg Gln Thr Pro Gly Lys Thr
        35                  40                  45

Leu Glu Trp Ile Gly Asp Ile Asn Ser Asp Gly Ser Ile Ile Asn Tyr
50                  55                  60

Ala Pro Ser Ile Lys Asp Arg Phe Thr Ile Phe Arg Asp Asn Asp Lys
65                  70                  75                  80

Thr Thr Leu Tyr Leu Gln Met Ser Asn Val Arg Ser Glu Asp Thr Ala
                85                  90                  95

Thr Tyr Phe Cys Ser Ile Tyr Tyr Asp Ser Trp Phe Ala Tyr Trp Gly
            100                 105                 110

Gln Gly Thr Leu Val Thr Val Ser Ala Ala Lys Thr Thr Pro Pro Ser
        115                 120                 125

Val Tyr Arg Ser Ser
    130

<210> SEQ ID NO 8
<211> LENGTH: 126
<212> TYPE: PRT
<213> ORGANISM: Artificial Sequence
<220> FEATURE:
<223> OTHER INFORMATION: Spike506-2G10G5 Kappa chain

<400> SEQUENCE: 8

Glu Leu Asp Ile Val Leu Thr Gln Ser Pro Leu Ser Leu Pro Val Ser
1               5                   10                  15

Leu Gly Asp Gln Ala Ser Ile Ser Cys Arg Ser Ser Gln Ser Ile Val

```
                20                  25                  30
His Ser Asn Gly Asn Thr Tyr Leu Glu Trp Tyr Leu Gln Lys Pro Gly
            35                  40                  45

Gln Ser Pro Lys Leu Leu Ile Tyr Lys Val Ser Asn Arg Phe Ser Gly
        50                  55                  60

Val Pro Asp Arg Phe Ser Gly Ser Gly Ser Gly Thr Asp Phe Thr Leu
 65                  70                  75                  80

Lys Ile Ser Arg Val Glu Ala Glu Asp Leu Gly Val Tyr Tyr Cys Phe
                85                  90                  95

Gln Gly Ser His Val Pro Arg Thr Phe Gly Gly Gly Thr Lys Leu Glu
            100                 105                 110

Ile Lys Arg Ala Asp Ala Ala Pro Thr Val Ser Ala Cys Thr
        115                 120                 125

<210> SEQ ID NO 9
<211> LENGTH: 25
<212> TYPE: PRT
<213> ORGANISM: MERS-CoV/KOR/KNIH/002_05_2015

<400> SEQUENCE: 9

Thr Lys Pro Leu Lys Tyr Ser Tyr Ile Asn Lys Cys Ser Arg Leu Leu
 1               5                  10                  15

Ser Asp Asp Arg Thr Glu Val Pro Gln
            20                  25

<210> SEQ ID NO 10
<211> LENGTH: 25
<212> TYPE: PRT
<213> ORGANISM: MERS-CoV/KOR/KNIH/002_05_2015

<400> SEQUENCE: 10

Thr Lys Pro Leu Lys Tyr Ser Tyr Ile Asn Lys Cys Ser Arg Phe Leu
 1               5                  10                  15

Ser Asp Asp Arg Thr Glu Val Pro Gln
            20                  25

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11
ggaagatctc ttgaccaggc atcctagagt ca                                    32

<210> SEQ ID NO 12
<211> LENGTH: 35
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t

<400> SEQUENCE: 12
cttccggaat tcsargtnma gctgsagsag tcwgg                                 35

<210> SEQ ID NO 13
<211> LENGTH: 30
```

```
<212> TYPE: DNA
<213> ORGANISM: Artificial Sequence
<220> FEATURE:
<223> OTHER INFORMATION: primer

<400> SEQUENCE: 13
ggtgcatgcg gatacagttg gtgcagcatc                                      30

<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
gggagctcga yattgtgmts acmcarwctm ca                                   32

<210> SEQ ID NO 15
<211> LENGTH: 399
<212> TYPE: DNA
<213> ORGANISM: Artificial Sequence
<220> FEATURE:
<223> OTHER INFORMATION: Spike506-2G10G5 Heavy chain

<400> SEQUENCE: 15
cttccggaat ccaagttaa gctgcaggag tctggaggag cttggtgca acctgggggg       60 tcacggggac tctcttgtga aggctcaggg tttacttta gtggcttctg gatgagctgg     120
gttcgacaga cacctggtaa gaccctggag tggattggag acattaattc tgatggcagt   180
ataataaact acgcaccatc catcaaggat cgattcacta tcttcagaga caatgacaag   240
accaccctgt acctgcagat gagcaatgtg cgatctgagg acacagccac gtatttctgt   300
tcgatctact atgattcctg gtttgcttac tggggccaag ggactctggt cactgtctct   360
gcagccaaaa cgacaccccc atctgtctat agatcttcc                           399

<210> SEQ ID NO 16
<211> LENGTH: 380
<212> TYPE: DNA
<213> ORGANISM: Artificial Sequence
<220> FEATURE:
<223> OTHER INFORMATION: Spike506-2G10G5 Kappa chain

<400> SEQUENCE: 16
gggagctcga tattgtgctc acacagtctc cactctccct gcccgtcagt cttggagatc    60
aagcctccat ctcttgcaga tctagtcaga gcattgtaca tagcaatgga aacacctatt   120
tagaatggta cctgcagaaa ccaggccagt ctccaaagct cctgatctac aaagtttcca   180
accgattttc tggggtccca gacaggttca gtggcagtgg atcagggaca gatttcacac   240
tcaagatcag cagagtggag gctgaagatc tgggagttta ttactgcttt caaggttcac   300
atgttcctcg acgttcggt ggaggcacca agctggaaat caaacgggct gatgctgcac    360
caactgtatc cgcatgcacc                                               380

<210> SEQ ID NO 17
<211> LENGTH: 465
<212> TYPE: DNA
<213> ORGANISM: Artificial Sequence
<220> FEATURE:
<223> OTHER INFORMATION: Spik492-1G10E4E2 Heavy chain

<400> SEQUENCE: 17
```

```
cttccggaat tccaagttca gctggagcag tctggggctg agctggtgag gcctggggct    60
tcagtgacgg tgtcctgcaa ggcttcgggc tacacattta ctgactatga aatgcactgg   120
gtgaagcaga cacctgtgca tggcctggaa tggattggag ctattgatcc tgaaactggt   180
ggtactgcct acaatcagaa gttcaagggc aaggccacac tgactgcaga caaatcctcc   240
agcacagcct acatggagct ccgcagcctg acatctgagg agtctgccgt ctattactgt   300
acaagaccaa gtagctacga tgctatggac tactggggtc aaggaacctc agtcaccgtc   360
tcctcagcca aaacaacagc cccatcggtc tatccactgg cccctgtgtg tggagataca   420
actggctcct cggtgactct aggatgcctg gtcaagagat cttcc                  465
```

<210> SEQ ID NO 18
<211> LENGTH: 155
<212> TYPE: PRT
<213> ORGANISM: Artificial Sequence
<220> FEATURE:
<223> OTHER INFORMATION: Spik492-1G10E4E2 Heavy chain

<400> SEQUENCE: 18

```
Leu Pro Glu Phe Gln Val Gln Leu Glu Gln Ser Gly Ala Glu Leu Val
1               5                   10                  15

Arg Pro Gly Ala Ser Val Thr Val Ser Cys Lys Ala Ser Gly Tyr Thr
            20                  25                  30

Phe Thr Asp Tyr Glu Met His Trp Val Lys Gln Thr Pro Val His Gly
        35                  40                  45

Leu Glu Trp Ile Gly Ala Ile Asp Pro Glu Thr Gly Gly Thr Ala Tyr
    50                  55                  60

Asn Gln Lys Phe Lys Gly Lys Ala Thr Leu Thr Ala Asp Lys Ser Ser
65                  70                  75                  80

Ser Thr Ala Tyr Met Glu Leu Arg Ser Leu Thr Ser Glu Glu Ser Ala
                85                  90                  95

Val Tyr Tyr Cys Thr Arg Pro Ser Ser Tyr Asp Ala Met Asp Tyr Trp
            100                 105                 110

Gly Gln Gly Thr Ser Val Thr Val Ser Ser Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys Arg Ser Ser
145                 150                 155
```

<210> SEQ ID NO 19
<211> LENGTH: 380
<212> TYPE: DNA
<213> ORGANISM: Artificial Sequence
<220> FEATURE:
<223> OTHER INFORMATION: Spik492-1G10E4E2 Kappa chain

<400> SEQUENCE: 19

```
gggagctcga tattgtgctg acacagtcta cactctccct gcctgtcagt cttgagatc    60 aagcctccat ctcttgcaga tctagtcaga gcattgtaca tagtaatgga aacacctatt   120
tagaatggta cctgcagaaa ccaggccagt ctccaaagct cctgatctac aaagtttcca   180
accgattttc tggggtccca gacaggttca gtggcagtgg atcagggaca gatttcacac   240
tcaagatcag cagagtggag gctgaggatc tgggaattta ttactgcttt caaggttcac   300
atgttccgta cacgttcgga ggggggacca agctggaaat aaaacgggct gatgctgcac   360
caactgtatc cgcatgcacc                                              380
```

```
<210> SEQ ID NO 20
<211> LENGTH: 126
<212> TYPE: PRT
<213> ORGANISM: Artificial Sequence
<220> FEATURE:
<223> OTHER INFORMATION: Spik492-1G10E4E2 Kappa chain

<400> SEQUENCE: 20

Glu Leu Asp Ile Val Leu Thr Gln Ser Thr Leu Ser Leu Pro Val Ser
1               5                   10                  15

Leu Gly Asp Gln Ala Ser Ile Ser Cys Arg Ser Ser Gln Ser Ile Val
            20                  25                  30

His Ser Asn Gly Asn Thr Tyr Leu Glu Trp Tyr Leu Gln Lys Pro Gly
        35                  40                  45

Gln Ser Pro Lys Leu Leu Ile Tyr Lys Val Ser Asn Arg Phe Ser Gly
    50                  55                  60

Val Pro Asp Arg Phe Ser Gly Ser Gly Ser Gly Thr Asp Phe Thr Leu
65                  70                  75                  80

Lys Ile Ser Arg Val Glu Ala Glu Asp Leu Gly Ile Tyr Tyr Cys Phe
                85                  90                  95

Gln Gly Ser His Val Pro Tyr Thr Phe Gly Gly Gly Thr Lys Leu Glu
            100                 105                 110

Ile Lys Arg Ala Asp Ala Ala Pro Thr Val Ser Ala Cys Thr
            115                 120                 125
```